United States Patent
Grubbs (10) Patent No.: US 10,517,992 B2
(45) Date of Patent: Dec. 31, 2019

(54) LIGHT-TRIGGERED SHAPE-CHANGEABLE HYDROGELS AND THEIR USE IN OPTICAL DEVICES

(71) Applicant: CALIFORNIA INSTITUTE OF TECHNOLOGY, Pasadena, CA (US)

(72) Inventor: Robert H. Grubbs, South Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 148 days.

(21) Appl. No.: 14/636,329

(22) Filed: Mar. 3, 2015

(65) Prior Publication Data
US 2015/0258240 A1 Sep. 17, 2015

Related U.S. Application Data

(60) Provisional application No. 61/952,280, filed on Mar. 13, 2014.

(51) Int. Cl.
*A61L 27/16* (2006.01)
*A61L 27/52* (2006.01)
*A61L 27/50* (2006.01)

(52) U.S. Cl.
CPC .............. *A61L 27/16* (2013.01); *A61L 27/50* (2013.01); *A61L 27/52* (2013.01); *A61L 2430/16* (2013.01)

(58) Field of Classification Search
CPC ......... A61L 27/16; A61L 27/50; A61L 27/52; A61L 2430/16; C08G 2210/00; Y10S 632/907; C08L 33/12
See application file for complete search history.

(56) References Cited

U.S. PATENT DOCUMENTS

| | | | |
|---|---|---|---|
| 7,789,910 B2 | 9/2010 | Knox et al. | |
| 8,604,098 B2 | 12/2013 | Boydston et al. | |
| 8,629,197 B2* | 1/2014 | Shoichet | C07D 311/16 424/400 |
| 8,933,143 B2 | 1/2015 | Boydston et al. | |
| 2008/0286360 A1 | 11/2008 | Schoichet et al. | |
| 2009/0157178 A1 | 6/2009 | Hampp | |
| 2011/0028667 A1* | 2/2011 | Ritter | C08F 224/00 526/270 |
| 2011/0092609 A1 | 4/2011 | Lendlein et al. | |
| 2012/0035293 A1* | 2/2012 | Boydston | A61F 2/14 522/99 |
| 2012/0228520 A1 | 9/2012 | Tan et al. | |
| 2013/0268072 A1 | 10/2013 | Smith et al. | |

(Continued)

FOREIGN PATENT DOCUMENTS

| | | | | |
|---|---|---|---|---|
| CN | 103204837 | * | 7/2013 | .......... C07D 311/16 |
| WO | WO 2010-103089 | * | 9/2010 | .............. A61F 2/14 |

OTHER PUBLICATIONS

Huang et al., machine English translation of CN 103204837 (pub Jul. 2014).*

(Continued)

*Primary Examiner* — Jessica M Roswell
(74) *Attorney, Agent, or Firm* — BakerHostetler (57) ABSTRACT

The present invention is directed to optical hydrogels, whose shape and/or refractive indices can be catalyzed by the application of light, methods of preparing the same, and optical devices and lenses derived therefrom.

38 Claims, 4 Drawing Sheets

(56) References Cited

U.S. PATENT DOCUMENTS

2014/0066537 A1\* 3/2014 Jerome .................. C08L 83/08
522/4
2015/0274885 A1\* 10/2015 Joy ...................... C07D 311/18
504/359

OTHER PUBLICATIONS

Machine English translation of WO 2010-103089; Ritter et al. (Sep. 2010).\*
Kim, et al., "Ophthalmic Drug Delivery Utilizing Two-Photon Absorption: A Novel Approach to Treat Posterior Capsule Opacification", SPIE BIOS, 2007, vol. 6632, 1-8.

\* cited by examiner

LIGHT-TRIGGERED SHAPE-CHANGEABLE HYDROGELS AND THEIR USE IN OPTICAL DEVICES

CROSS REFERENCE TO RELATED APPLICATIONS

This application claims the benefit of priority to U.S. Provisional Application Ser. No. 61/952,280, filed Mar. 13, 2014, the subject matter of which is incorporated by reference herein in its entirety for all purposes.

TECHNICAL FIELD

This invention disclosure is directed to shape-changing hydrogels, the shape-change catalyzed by the application of light, methods of preparing the same, and optical devices and lenses derived therefrom.

BACKGROUND

The insertion of an intraocular lens is a common eye surgical procedure for the treatment of cataracts, or as a form of refractive surgery to change the eye's optical power and decrease or eliminate dependency on glasses or contact lenses. Successful refractive eye surgery can reduce or cure common vision disorders such as myopia, hyperopia and astigmatism.

For certain applications, healing alters the physical environment around the lens. Lens adjustment via photoinitiated polymerization can account for the changes in the physical environment. During the healing time, premature polymerization of the lens material (e.g. from exposure to sunlight) can be detrimental to the procedure.

As such, lenses and pre-polymer materials that resist polymerization in sunlight during healing but which can be readily polymerized on demand are of interest.

SUMMARY

The present invention is directed to optical hydrogels, whose shape and/or refractive indices can be catalyzed by the application of light, methods of preparing the same, and optical devices and lenses derived therefrom. Further, the invention relates to optical devices, including intraocular lenses, whose refractive indices can be changed by an external light source after the healing process associated with implantation of the lens(es) is complete. The lens is stable until a pattern of light of the proper wave-length is used to change the power of the lens. In certain preferred embodiments, the process used to affect these changes will be a two-photon process that requires a fast laser system.

Certain embodiments provide optical hydrogel compositions comprising at least one hydrophilic polymer or copolymer prepared from acrylate, methacrylate, or both acrylate and methacrylate monomers, the hydrophilic polymer or copolymer being crosslinked with photocleavable linkages; said composition being deformable upon cleavage of the photocleavable linkages. In some embodiments, the compositions further comprises a reversibly photoisomerizable photomasking compound that interconverts between a first and second photoisomer upon application of light, wherein the first isomer absorbs more light at the at least one activating wavelength of light than does the second isomer. In independent sub-embodiments, (a) the hydrogel comprises water in an amount in a range from about 10 wt % to about 50 wt %, relative to the weight of the entire hydrogel composition; (b) the water is uniformly or periodically distributed throughout the hydrogel; (c) said composition is transparent to at least one wavelength and preferably a range of wavelengths of light in a range of from about 200 and about 1000 nm; (d) said photocleavable linkages being receptive to cleavage with an application of at least one activating wavelength of light in a range of from about 200 nm and about 1000 nm (1 micron); or (d) a combination of at least two of (a), (b), (c), and (d).

In many embodiments, the photocleavable linkages are receptive to photocleavage by an application of a double or multiple photon irradiation ("multiphoton excitation"), for example comprising at least one coumarin moiety, nitrobenzyl-ether moiety, nitroindoline-ether moiety, or p-hydroxyphenacyl moiety, or a combination thereof.

In other embodiments, these optical hydrogel compositions may be configured and suitable for use as optical devices in human patients, non-limiting examples of these optical devices being intraocular lenses, corneal inlays, corneal rings, or keratoprotheses. In some embodiments, these optical devices are surgically implanted or otherwise positioned within the eye of the patient.

The present invention is also directed to methods of altering the shapes and/or optical characteristics these optical hydrogel compositions or devices using light, and the resulting compositions or devices. For example, certain methods provide for irradiating the inventive optical hydrogel composition or devices with at least one suitable wavelength of light in a range of from about 200 nm to about 1 micron, with sufficient power and duration, so as to cleave at least a portion of the photocleavable linkages within a pre-determined volume of the hydrogel. Upon cleavage of these linkages, the initially distributed water is re-distributed within the hydrogel, in some cases providing three-dimensional pockets, channels, or layers of higher concentrations of water, resulting in a deformation of the shape, a change in the refractive index, or both deformation and change of refractive index of the of the composition or device, relative to its initial state. In some cases, the irradiation may be applied by a laser of sufficient character that it can be done while the optical device is implanted in the patient. Preferably the laser is capable of providing a two or multi-photon light source.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings.

DETAILED DESCRIPTION OF ILLUSTRATIVE EMBODIMENTS

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiments to embodiments in each and every one of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The terms "optional" or "optionally" means that the subsequently described circumstance may or may not occur, so that the description includes instances where the circumstance occurs and instances where it does not. For example, the phrase "optionally deformable" means that a hydrogel may or may not actually deform (at least to any perceptible extent), despite a redistribution of water within the hydrogel following irradiation. Thus, the description "optional" allows for, but does not require, the optional condition to occur.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of," the basic and novel characteristic(s) is the facile operability of the methods (or the systems used in such methods or the compositions derived therefrom) to change the shape or refractive indices (or both) of hydrogels using the application of light to modify the character of the hydrogel and concomitant re-distribution of water within the hydrogel.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Certain embodiments of the present invention include those optical hydrogel compositions comprising:

at least one hydrophilic polymer or copolymer prepared from acrylate, methacrylate, or both acrylate and methacrylate monomers, the hydrophilic polymer or copolymer being crosslinked with photocleavable linkages;

the hydrogel comprising water in an amount in a range from about 10 wt % to about 50 wt %, relative to the weight of the entire hydrogel composition;

said composition being transparent to at least one wavelength of light in a range of from about 200 and about 1000 nm; and said photocleavable linkages being receptive to cleavage with an application of at least one activating wavelength of light in a range of from about 200 nm and about 1000 nm (1 micron). In some embodiments, the at least one activating wavelength of light is present in a range of from about 200 nm to about 300 nm, from about 300 nm to about 400 nm, from about 500 nm to about 600 nm, from about 600 nm to about 700 nm, from about 700 nm to about 800 nm, from about 800 nm to about 900 nm, from about 900 nm to about 1000 nm (1 micron), or any combination of two or more of these ranges. Other specific wavelengths are described herein. In some embodiments, the compositions are optionally deformable upon cleavage of the photocleavable linkages and redistribution of water within the hydrogel.

As used herein, the term "optical hydrogels" is used to connote a hydrogel composition have physical properties, including biocompatibility and optical characteristics (e.g., visual clarity), suitable for use in optical devices. But it should be appreciated that the principles described herein (e.g., changing of shape or optical property based on redistribution of a liquid phase within a gel following the selective change in crosslink density by application of electromagnetic radiation) are suitable also for use in other gel compositions, and these other compositions are also considered within the scope of the present invention.

Figure 1A:
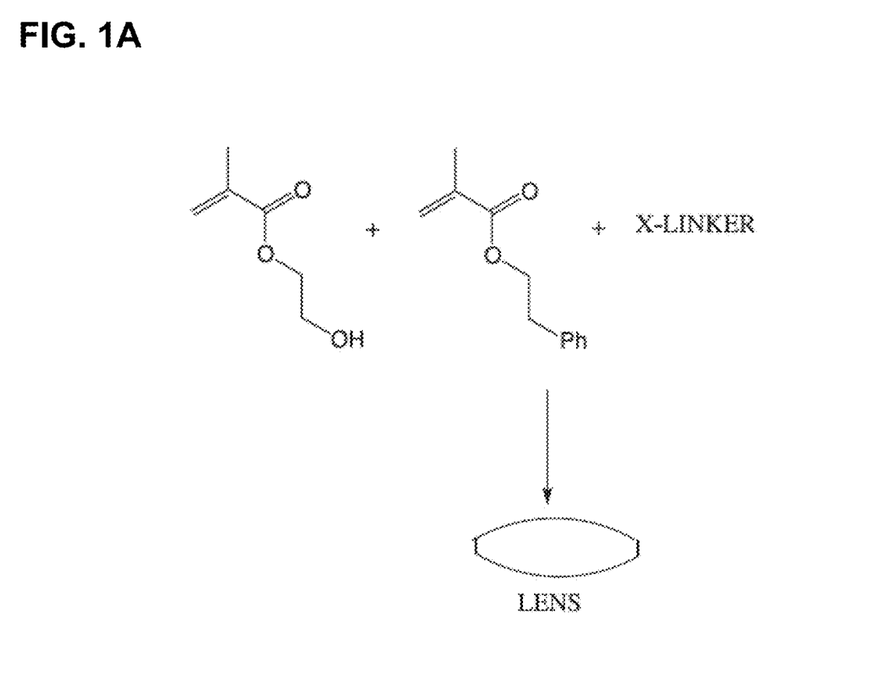
FIG. 1A shows a schematic representation of a two suitable (meth)acrylates forming a lens.
Figure 1B:
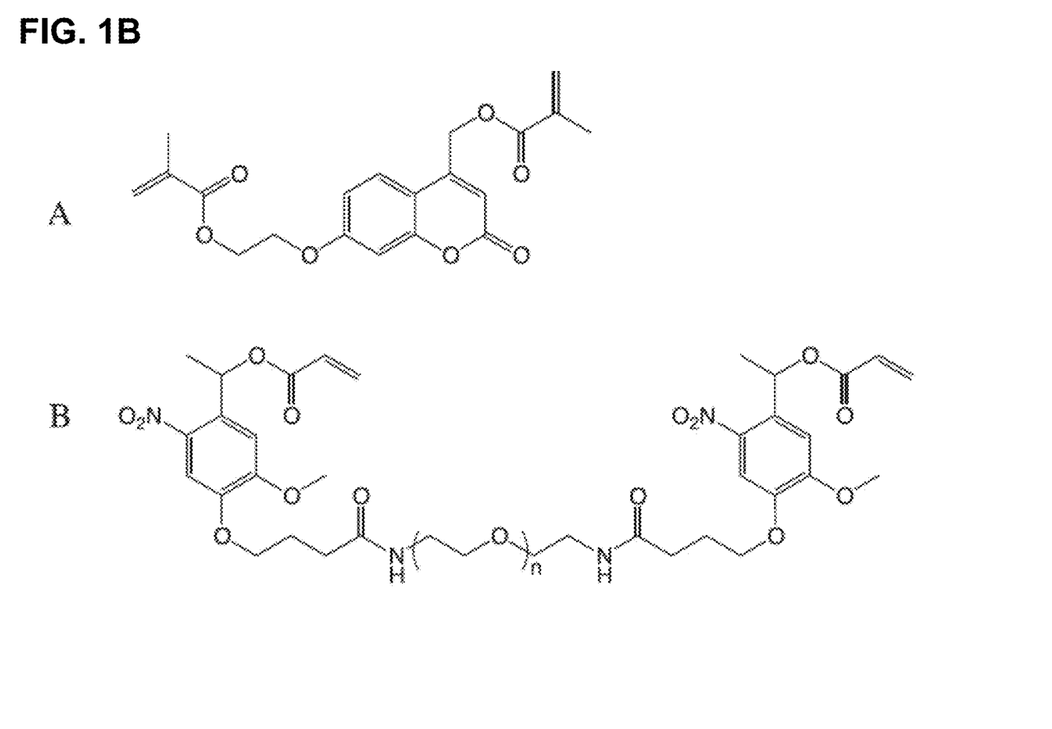
FIG. 1B shows examples of possible cross-linkers: A. Coumarin-based cross-linker; and B. 2-nitrobenzene based cross-linker.

The hydrogels may comprise any hydrophilic polymer system capable of sustaining a hydrogel structure, but in preferred embodiments, as one important application of this technology is its use in optical devices, implanted into human patients, the polymers and hydrogels are compatible and suitable for use in such applications. Further, these hydrogels may comprise polymers prepared from biocompatible materials including acrylate, methacrylate, or both acrylate and methacrylate monomers. As used herein, the term "(meth)acrylate" refers to materials that include acrylate, methacrylate, or both acrylate and methacrylate monomers, as is recognized in the art for such materials. In more preferred embodiments, the acrylates or methacrylates (i.e., "(meth)acrylates") are substituted with water compatible functionalities, such as hydroalkyl (e.g., hydroxymethyl, hydroxyethyl, or hydroxypropyl) groups. Nonhydrophilic monomers can be used to help to modify the hydrophilicity and the refractive index of the polymer materials, and in the case of (meth)acrylate polymers, hydrophobic acrylates/methacrylates can be used to tune these properties. Exemplary suitable (meth)acrylates include 2-hydroxymethyl (meth)acrylate, 2-hydroxyethyl(meth)acrylate, methyl-2-(hydroxymethyl)(meth)acrylate, ethyl 2-(hydroxymethyl) (meth)acrylate, 2-phenylethyl(meth)acrylate, methyl(meth) acrylate and 3-phenylpropyl(meth)acrylate. See, e.g., FIG. 1A and FIG. 1B.

The hydrogels of the present invention are crosslinked, at least some of the crosslinkers comprising photocleavable linkages. This allows selective cleavage and accompanying change in crosslink density of the hydrogel, which in turns can affect the shape and refractive indices of the materials. Such linkages may be chosen so as to be photocleavable with any source of electromagnetic radiation, particularly light. Preferably the linkages are chosen to as to be photocleavable with confocal sources of light, for example multiphoton irradiation, allowing for selective cleavage of the linkages anywhere in the body of the hydrogel or optical device comprising the hydrogel. One particularly attractive system for accomplishing this is to use photocleavable linkages that are receptive to photocleavage by an application of double or multiple photon irradiation. Multiphoton irradiation provides for the near simultaneous absorption of two or more low-energy photons so as to provide an energy level that is otherwise accessible only by high energy lasers. This method is particularly attractive because of its confocal nature, which provides for the ability to focus the energy with 3-dimensional precision in an object, in this case the hydrogel. Further, this technique provides that the high energy is focused only in a small volume around the focal point of the irradiating laser so that the irradiation is limited to the specific targeted areas or volumes, without changing or damaging the surrounding materials.

The chemistries associated with such multiple excitation/irradiation include those comprising coumarins, ortho-nitrobenzyl alcohols or ethers, nitroindoline alcohols or ethers, or p-hydroxyphenacyl moieties and in the present invention, linkages comprising one or more of these types of functional groups are preferred. These can be incorporated into the hydrogel matrices either by incorporating the precursors into the polymer backbones and subsequently crosslinking them, or by polymerizing materials directly along with the prepolymer monomers. For example, in the case of (meth) acrylate polymers, a desirable crosslinked hydrogel may be obtained by copolymerizing (meth)acrylate monomers with one or more compounds having a structure such as:

where n is an integer in a range of from 1 to 100. Obviously, the crosslink density affects the physical character of the resulting polymer, and the person of ordinary skill would be able to tune the properties as desired without undue experimentation.

Importantly, the crosslink density affects the amount and distribution of water within the hydrogel matrix. In preferred embodiments, the optical hydrogel composition comprises water in a range of from about 5 wt % to about 10 wt %, from about 10 wt % to about 20 wt %, from about 20 wt % to about 30 wt %, from about 30 wt % to about 40 wt %, from about 40 wt % to about 50 wt %, from about 50 wt % to about 60 wt %, or any combination of two or more of these ranges, where weight percent is relative to the weight of the entire optical hydrogel composition. In preferred embodiments, water is present in a range of from about 10 wt % to about 50 wt %. In some embodiments, the water may be present anisotropically (i.e., present as a continuous or discontinuous gradient) within a body of the hydrogel composition. For example, if the hydrogel is in the form of a flat or curved sheet, or in the form of a lens, characterized by having two (or more) surfaces, the crosslink densities may be higher closer to one surface than another surface, or may be higher or lower at each or all surfaces relative to the density between the surfaces, depending on the manner of manufacture. This change in crosslink density would be expected, then, to have a corresponding inverse effect on the concentration of water within the body of such a structure. In some embodiments, though, the water in these hydrogel compositions is distributed substantially uniformly throughout a body of the hydrogel composition. The term "substantially uniformly" allows for some microscopic variances across the hydrogel, but connotes that these variances are relatively unimportant to the utility of a device containing the hydrogel on a macroscopic scale.

The chemistry of the crosslinking moieties is also such that their cleavage can also be affected by irradiation with higher energy UV or visible light, either deliberately through the use of focused light source or, in some cases, by ambient light of appropriate wavelength. So as to avoid inadvertent cleavage of these linkages, for example when the compositions or corresponding optical devices are exposed to ambient light, in some embodiments, the inventive optical hydrogel compositions may further comprise a photomasking compound that absorbs wavelengths of light in a range of from about 200 nm to about 365 nm. In some embodiments, the photomasking compound comprises a benzotriazole moiety (see, e.g., FIG. 5). In some embodiments, this photomasking compound is a reversibly photoisomerizable photomasking compound that interconverts between a first and second photoisomer upon application of light, wherein the first isomer absorbs more light at the at least one activating wavelength of light than does the second isomer. Such photoisomers, and their principles of operations, are described in U.S. Pat. Nos. 8,604,098 and 8,933,143, the contents of which are incorporated herein by reference at least for descriptions of such photomasking structures and their methods of use. In such compositions, the photomasking compound is generally capable of photoisomerization between a first isomer and a second isomer upon absorption of electromagnetic energy at a first wavelength and intensity; preferably, in the present case, the photomasking compound is present in an amount sufficient to block cleavage of the photocleavable linkage unless or until the photomasking compound is photoisomerized from the first isomer to the second isomer. Such photoisomerizable photomasking compounds may operate by a cis-trans, cyclization, or ring-opening transformation, and include compounds such as azoarylenes, fulgides, spiropyrans, naphthopyrans, quinones, spirooxazines, nitrones, thioindigos, diarylethenes, or dithienylethylenes.

As described herein, certain embodiments of the present invention provide that these optical hydrogel compositions are configured and suitable for use as an optical device, optionally designed for implanting into human patients. Such optical devices include intraocular lenses, corneal inlays, corneal rings, or a keratoprotheses. These devices may be also positioned in the lens capsule of a patient. These optical devices can be prepared using techniques similar to those now utilized for the manufacture of comparable currently available optical devices, for example hydrophilic intraocular lenses. With appropriate cross-link density and water content, as described herein, the lens can be molded to provide foldable lens of a variety of powers and manufactured with standard haptics.

Again, the presence of the photocleavable crosslinking moieties provides the ability to alter the shape and optical characteristics these optical hydrogel compositions or devices using light, and the methods for accomplishing these transformations and resulting structures are also within the scope of the present invention.

For example, certain embodiments of the present invention include those methods of modifying the refractive index of an optical device, said optical device comprising an optical hydrogel composition, said optical device or optical hydrogel comprising any of the devices or hydrogels described herein, the method comprising irradiating the optical hydrogel composition with at least one wavelength of light in a range of from about 200 nm to about 1 micron (or any one or more of the sub-ranges of this broader range described herein), so as to cleave at least a portion of the photocleavable linkages. This irradiation may be accomplished using directed focus of UV-Vis or multiphoton near-IR wavelengths, at powers and for durations sufficient to cleave the requisite number of photocleavable linkages (as determined by the desired property change, e.g., refractive index) to affect the desired change in the hydrogel. Lasers currently considered useful for LASIK or cataract surgeries are expected to be useful in the instant application. In such treatments, the laser may apply a pulse energy in a range of from about 0.05 nJ to 1000 nJ, or sub-ranges within this range (e.g., from about 0.2 nJ to about 100 nJ and from about 0.5 to about 10 nJ). In such treatments, the laser provides a pulse having a duration in a range of from about 1 femtoseconds to about 500 femtoseconds, preferably from about 4 to about 100 femtoseconds. Such pulse powers and durations are believed to be appropriate in the instantly described optical hydrogels.

Figure 2A:
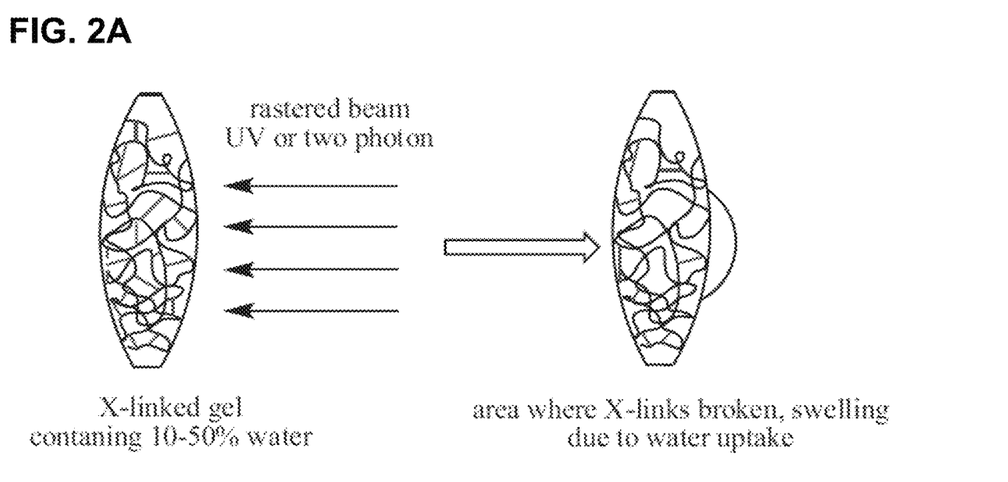
FIG. 2A illustrates a principle of the present invention.
Figure 2B:
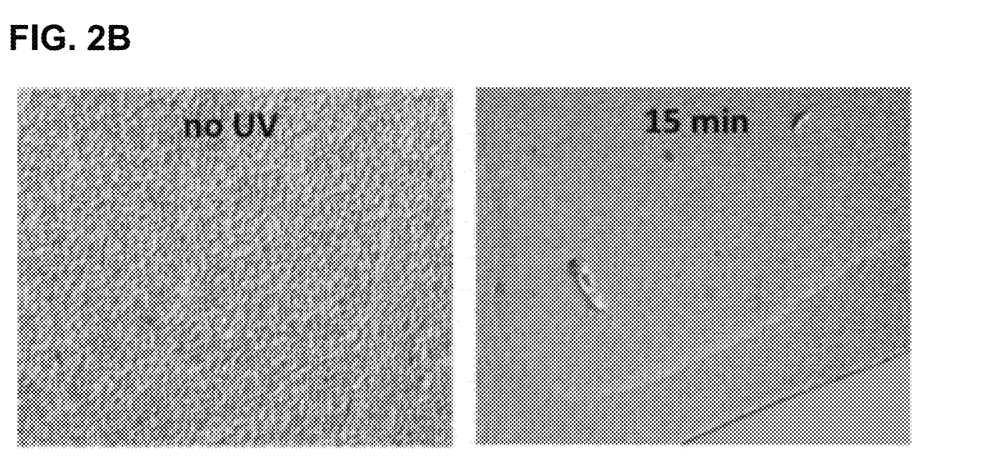
FIG. 2B shows micrographs of hydrogel loaded with 10% of crosslinker before (left) and after 15 min irradiation at 365 nm (right) through a photomask.

In the case of lenses or other optical devices, this can be used to adjust the optical properties of the devices in predetermined ways. Selective and focused cleavage of these photolabile linkages, and so the local crosslink density, results in the redistribution of water within the hydrogel structure, which in turn will produce a change in the refractive power of the lens, as the irradiated region of the hydrogel takes up more water. Since water and the matrix material have a different refractive indices, this region of the lens will change power as the shape of the lens changes. (FIG. 2A). Irradiation of a lens loaded with 10% of coumarin-based cross-linker at 365 nm resulted in a detectable shape change (FIG. 2B).

The use of lasers, especially confocal multiphoton lasers, are particular suited for these methods, allowing for the precise and focused irradiation and three-dimensional control of irradiation within the hydrogel matrices, without damaging the other portions of the compositions or devices. In this way, it is possible to tailor the changes within the hydrogels in three dimensions, for example producing three-dimensional optionally overlaid pockets, channels, or layers of lower crosslink density/higher concentrations of water so as to affect precise control of changes to the refractive indices.

Certain sub-embodiments also provide methods wherein the method is performed following the surgical insertion of the optical device in a human eye. Other sub-embodiments provide that the methods further comprising verifying a change in refractive index of the optical hydrogel composition. Each of the inventive methods may be repeated one or more times after checking the effect of preceding irradiations. Subsequent irradiations may be applied in the same or different portions of the optical hydrogels or devices for more precise tuning.

For those compositions comprising the photomasking photoisomers, methods may further comprise applying sufficient electromagnetic energy of a first wavelength to cause photoisomerization of a photomasking compound before applying the photocleavage of the photocleavable linkages, such that the photoisomerization converts the photomasking compound from a first photoisomer to a second photoisomer, and wherein the second photoisomer absorbs less light at the second wavelength than does the first photoisomer. The photoisomerization may comprise a cis-trans, cyclization, or ring-opening transition within the photomasking compound.

As described above, the irradiated compositions, derived from the initial compositions using the described methods also are within the scope of the present invention. For the sake of completeness, such embodiments include those optical devices derived from any of the hydrogel composition described herein, any one of which has been irradiated by a focused, near IR, visible, or UV light source so as to cleave at least a portion of the photocleavable linkages. The degree of such photocleavage should be sufficient to affect a real change in some physical characteristic of the optical hydrogel, for example crosslink density, shape, or refractive index. A change in the crosslink density within that optical hydrogel portion of the optical devices allows a redistribution of water within the optical hydrogel composition. Relative to the pre-irradiated compositions, cleaving at least a portion of the photocleavable linkages may result in a deformation or change of shape of the optical hydrogel composition. Such deformation may occur or may be imperceptible or prevented by some constraint external to the hydrogel body. Cleaving at least a portion of the photocleavable linkages may result in change of refractive index of the optical hydrogel. Such would be the expected consequence of the change in crosslink density and association redistribution of water within the hydrogel. The irradiated optical device may be defined in terms of additional three-dimensional pockets, channels, or layers, internal to the body of the hydrogel, and optionally overlaid on one another, which were otherwise not present in the original, pre-irradiated structure.

The following listing of embodiments is intended to complement, rather than displace or supersede, the previous descriptions.

Embodiment 1

A optical hydrogel composition comprising:
at least one hydrophilic polymer or copolymer prepared from acrylate, methacrylate, or both acrylate and methacrylate monomers, the hydrophilic polymer or copolymer being crosslinked with photocleavable linkages;
the hydrogel comprising water in an amount in a range from about 10 wt % to about 50 wt %, relative to the weight of the entire hydrogel composition;
said composition being transparent to at least one wavelength of light in a range of from about 200 and about 1000 nm or about 365 nm to about 1000 nm; and
said photocleavable linkages being receptive to cleavage with an application of at least one activating wavelength of light in a range of from about 200 nm to about 300 nm, from about 300 nm to about 400 nm, from about 500 nm to about 600 nm, from about 600 nm to about 700 nm, from about 700 nm to about 800 nm, from about 800 nm to about 900 nm, from about 900 nm to about 1000 nm (1 micron), or any combination of two or more of these ranges. In some embodiments, the compositions are deformable upon cleavage of the photocleavable linkages and redistribution of water within the hydrogel.

Embodiment 2

The composition of Embodiment 1, further comprising a photomasking compound that absorbs wavelengths of light in a range of from about 200 nm to about 365 nm. In some embodiments, the photomasking compound comprises a benzotriazole moiety.

Embodiment 3

The composition of Embodiment 2, wherein the photomasking compound is a reversibly photoisomerizable photomasking compound that interconverts between a first and second photoisomer upon application of light, wherein the first isomer absorbs more light at the at least one activating wavelength of light than does the second isomer.

Embodiment 4

The composition of any one of Embodiments 1 to 3, wherein the acrylate or methacrylate monomers are substituted with hydroxymethyl, hydroxyethyl, or hydroxypropyl groups.

Embodiment 5

The composition of any one of Embodiments 1 to 4, wherein the acrylate or methacrylate monomers comprise 22-hydroxymethyl(meth)acrylate, 2-hydroxyethyl(meth)acrylate, methyl-2-(hydroxymethyl)(meth)acrylate, or ethyl 2-(hydroxymethyl)(meth)acrylate.

Embodiment 6

The composition of any one of Embodiments 1 to 5, wherein the photocleavable linkages are receptive to photocleavage by an application of a double or multiple photon irradiation. In some of these embodiments, the photocleavable linkages may be described as susceptible to multiphoton excitation.

Embodiment 7

The composition of any one of Embodiments 1 to 6, wherein the photocleavable linkages comprise coumarin moieties, nitrobenzyl-ether moieties, nitroindoline-ether moieties, p-hydroxyphenacyl moieties, or a combination thereof.

Embodiment 8

The composition of any one of Embodiments 1 to 7, wherein the at least one hydrophilic polymer or copolymer is prepared by copolymerizing acrylate, methacrylate, or both acrylate and methacrylate monomers with one or more compounds having a structure:

where n is an integer in a range of from 1 to 100.

Embodiment 9

The composition of any one of Embodiments 1 to 8, wherein the water is uniformly distributed throughout the hydrogel throughout the hydrogel.

Embodiment 10

The composition of any one of Embodiments 1 to 9, wherein the optical hydrogel composition is configured and suitable for use as an intraocular lens, a corneal inlay, a corneal ring, or a keratoprothesis in a human patient.

Embodiment 11

The composition of Embodiments 1 to 10, wherein the optical hydrogel composition has been positioned in the lens capsule of a patient.

Embodiment 12

An optical device derived from the hydrogel composition of any one of Embodiments 1 to 11, which has been irradiated by a focused, near IR, visible, or UV light source so as to cleave at least a portion of the photocleavable linkages, allowing a redistribution of water within the optical hydrogel composition.

Embodiment 13

The optical device of Embodiment 12, wherein cleaving at least a portion of the photocleavable linkages results in a deformation or change of shape of the optical hydrogel composition.

Embodiment 14

The optical device of Embodiment 121 or 13, wherein the cleaving at least a portion of the photocleavable linkages results in change of refractive index of the optical hydrogel composition.

Embodiment 15

The optical device of Embodiment 12, wherein the light source provides a two or multiple photon source Embodiment 16

The optical device of Embodiment 12, wherein the redistribution of water causes the optical hydrogel to deform, such that the irradiated device has a shape that is different than that of the pre-irradiated device.

Embodiment 17

An optical device comprising the optical polymeric hydrogel of any one of Embodiments 1 to 11, in which at least a portion of the photocleavable linkages have been cleaved by irradiation with light, preferably by a multiphoton process.

Embodiment 18

The optical device of any one of Embodiments 12 to 17, wherein the irradiated regions of the optical device are defined by a three dimensional structure within the hydrogel composition.

Embodiment 19

The optical device of any one of Embodiments 12 to 18, wherein the irradiated device exhibits a refractive index that is different than that of the pre-irradiated device.

Embodiment 20

The optical device of any one of Embodiments 12 to 19, wherein light source is a laser.

Embodiment 21

The optical device of Embodiment 20, wherein the laser is suitable for use on human patients.

Embodiment 22

The optical device of Embodiment 20 or 21, wherein the laser provides a pulse energy in a range of from about 0.05 nJ to 1000 nJ.

Embodiment 23

The optical device of any one of Embodiments 20 to 22, wherein the laser provides a pulse having a duration in a range of from about 1 femtoseconds to about 500 femtoseconds, preferably from about 4 to about 100 femtoseconds.

Embodiment 24

A method for modifying the refractive index of an optical device, said optical device comprising an optical hydrogel composition (such as described in Embodiments 1 to 11, but also) comprising:

at least one hydrophilic polymer or copolymer prepared from acrylate, methacrylate, or both acrylate and methacrylate monomers, the hydrophilic polymer or copolymer being crosslinked with photocleavable linkages;

the hydrogel comprising water in an amount in a range from about 10 wt % to about 50 wt %, relative to the weight of the entire hydrogel composition;

said composition being transparent to at least one wavelength of light in a range of from about 200 and about 1000 nm; and said photocleavable linkages being receptive to cleavage with an application of at least one activating wavelength of light in a range of from about 200 nm and about 1000 nm (1 micron). In some embodiments, the composition is deformable upon cleavage of the photocleavable linkages and redistribution of water within the hydrogel;

the method comprising irradiating the optical hydrogel composition with at least one wavelength of light in a range of from about 200 nm to about 1 micron, so as to cleave at least a portion of the photocleavable linkages.

Embodiment 25

The method of Embodiment 24, wherein cleaving at least a portion of the photocleavable linkages results in a redistribution of water within the optical hydrogel composition.

Embodiment 26

The method of Embodiment 24 or 25, wherein cleaving at least a portion of the photocleavable linkages results in a deformation or change of shape of the optical hydrogel composition.

Embodiment 27

The method of any one of Embodiments 24 to 26, wherein the cleaving at least a portion of the photocleavable linkages results in change of refractive index of the optical hydrogel composition.

Embodiment 28

The method of any one of Embodiments 24 to 27, wherein the irradiating light is provided by a laser.

Embodiment 29

The method of any one of Embodiments 24 to 28, wherein the irradiating light is provided by a two or multi-photon light source.

Embodiment 30

The method of any one of Embodiments 24 to 29, wherein the irradiated regions of the optical device are defined by a three dimensional structure within the hydrogel composition.

Embodiment 31

The method of any one of Embodiment 24 to 30, wherein the method is performed following the surgical insertion of the optical device in a human eye.

Embodiment 32

The method of any one of Embodiment 24 to 31, further comprising verifying a change in refractive index of the optical hydrogel composition.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

Example 1

The selective photocleavage is demonstrated by the use of UV light. However, for a lens in the eye, a laser is used to produce two or multiple photon chemistry. In the prepared lens, a standard UV block is added to prevent transformation by normal daylight. The lasers used in LASIK surgery that are now being developed for use in cataract surgery are used for the change in the lens power through cross link cleavage and swelling. The change requires precise control of the beam that may be defocused to produce a larger zone and only give photocleavage rather that material destruction.

Example 2

In another system, the cross-linker is cleaved by light in the 365 range so that there is easy access through the cornea. In this approach, a reversible UV-block is used that bleaches at 365 nm but then returns to a blocking state under the usual range of wave lengths or a selective wave length that isomerizes the block back to a blocking state in the region of absorption of the cross linker chromaphore. Azobenzene and stilbene derivatives are used in such situations (FIG. 3A/B and FIG. 4).

Example 3

Figure 3:
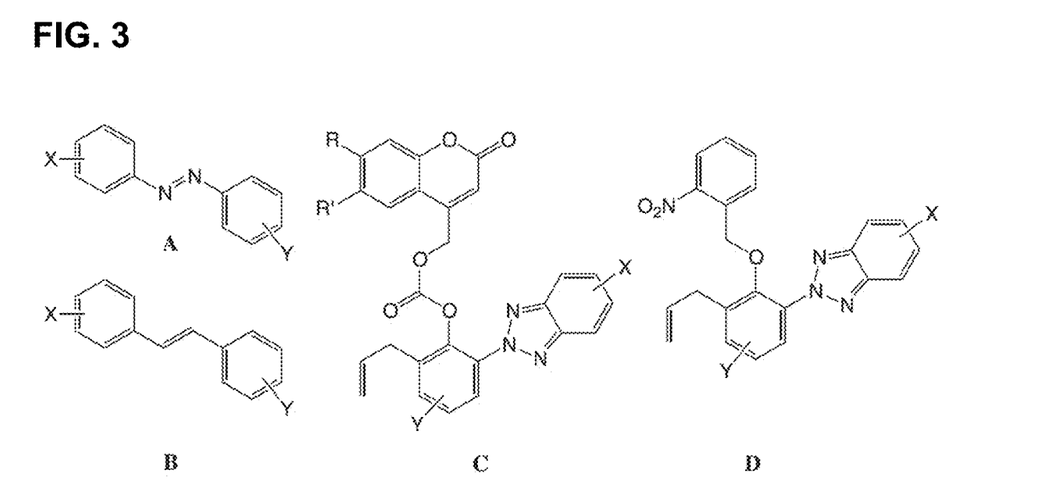
FIG. 3 shows examples of structures of reversible and caged UV-blocks.
Figure 4:
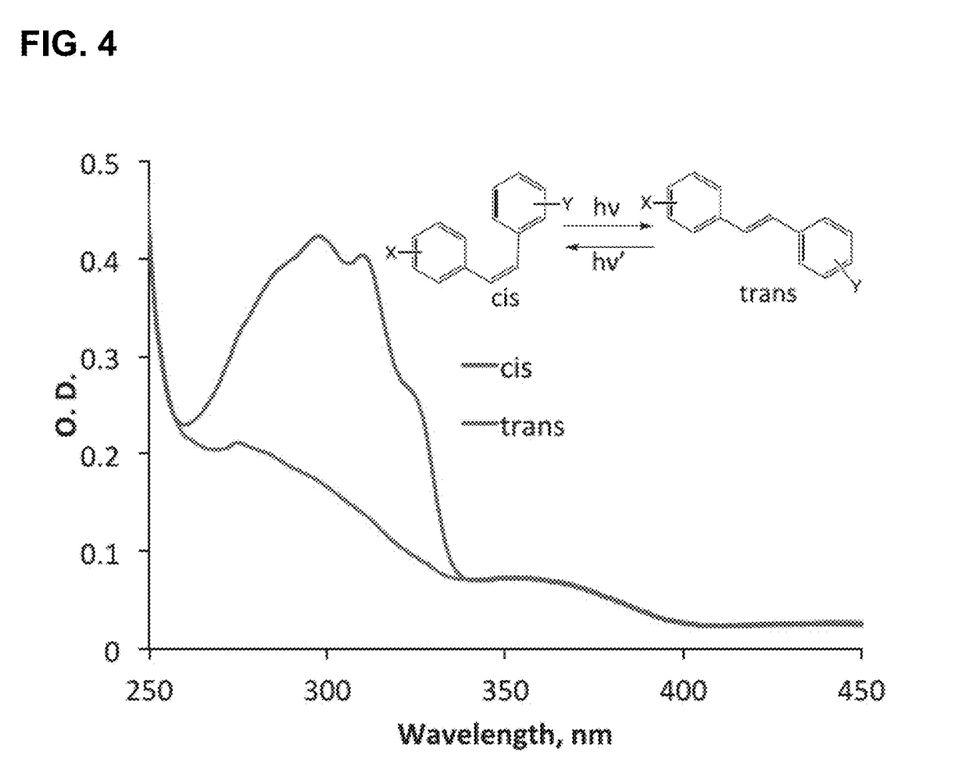
FIG. 4 shows an exemplary spectrum of a stilbene-photoisomerizable UV-block
Figure 5:
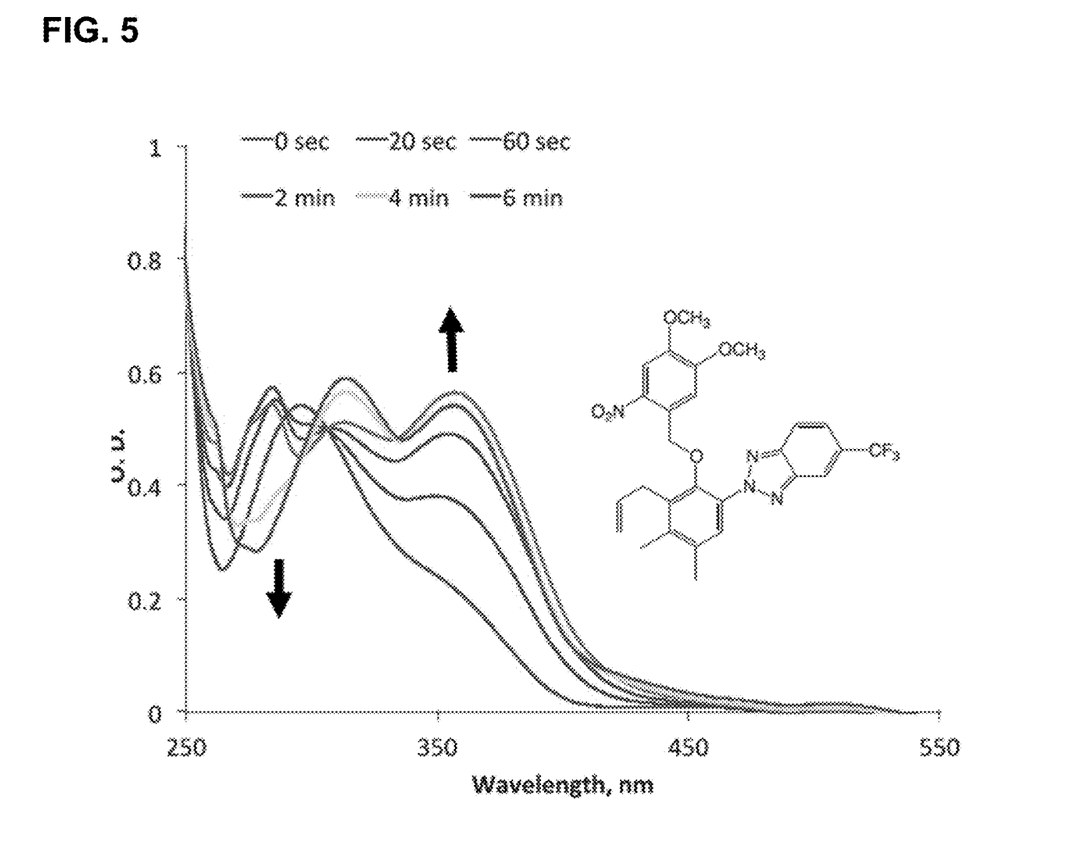
FIG. 5 shows a photolysis profile of benzotriazole-type UV-block, caged with dimethoxy nitrobenzyl moiety. Cage removal results in absorption maximum shift from 297 nm to 315 nm and 357 nm. Arrows point in direction of increasing time.

An alternative approach is to use a caged UV-block that releases at a wave length different from the one used to do the cleavage of the cross linker (FIG. 3C and FIG. 3D). A photolysis profile of a potential caged UV-block—benzotriazole, modified with 4,5-dimethoxy-2-nitrobenzyl ether cage is represented in FIG. 5.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

The following references may be useful in understanding some elements of the present invention or background principles thereof.
1. J. Trager, H. C. Kim N. Hampp. SPIE BIOS 2006, 1-9.
2. U.S. Pat. No. 7,789,910 B2 to W. H. Knox, et al., (Bausch & Lomb Incorporated)

What is claimed:
1. An optical device comprising an optical hydrogel composition, the optical hydrogel composition comprising:
   at least one hydrophilic (meth)acrylate polymer or copolymer and at least one hydrophobic (meth)acrylate polymer or copolymer, wherein the hydrophilic and/or hydrophobic polymer or copolymer are crosslinked with photocleavable linkages;
   said optical hydrogel composition being transparent to at least one wavelength of light in a range of from about 200 to about 1000 nm; and
   said photocleavable linkages being receptive to cleavage with an application of at least one activating wavelength of light in a range of from about 200 nm and about 1000 nm;
   wherein the photocleavable linkages:
   (a) comprise a nitrobenzyl-ether moiety, a nitroindoline-ether moiety, a p-hydroxyphenacyl moiety, or a combination thereof; or
   (b) are prepared by copolymerizing (meth)acrylate monomers with a compound having a structure:

or
   (c) are a combination of both (a) and (b).

2. An optical device comprising an optical hydrogel composition, the optical hydrogel composition comprising
   at least one hydrophilic (meth)acrylate polymer or copolymer and at least one hydrophobic (meth)acrylate polymer or copolymer, wherein the hydrophilic and/or hydrophobic polymer or copolymer are crosslinked with photocleavable linkages, wherein the photocleavable linkages comprise a coumarin moiety, a nitrobenzyl-ether moiety, a nitroindoline-ether moiety, or a p-hydroxyphenacyl moiety, or a combination thereof,
   the optical hydrogel composition containing separate regions of different crosslink densities resulting from the selective cleavage of the photocleavable linkages in the separate regions of the optical hydrogel composition; and
   wherein:
   (a) the optical hydrogel composition is transparent to at least one wavelength of light in a range of from about 200 to about 1000 nm;
   (b) the photocleavable linkages are receptive to cleavage with an application of at least one activating wavelength of light in a range of from about 200 nm and about 1000 nm; and
   (c) the separate regions of different crosslink densities contain different distributions of water.

3. The optical device of claim 2, further comprising a photomasking compound that absorbs wavelengths of light in a range of from about 200 nm to about 365 nm.

4. The optical device of claim 3, wherein the photomasking compound is a reversibly photoisomerizable photomasking compound that interconverts between a first and second photoisomer upon application of light, wherein the first isomer absorbs more light at the at least one activating wavelength of light than does the second isomer.

5. The optical device of claim 2, wherein the at least one hydrophilic or hydrophobic (meth)acrylate polymer or copolymer is substituted with hydroxymethyl, hydroxyethyl, or hydroxypropyl groups.

6. The optical device of claim 1, wherein the at least one hydrophilic or hydrophobic (meth)acrylate polymer or copolymer is substituted with hydroxymethyl, hydroxyethyl, or hydroxypropyl groups.

7. The optical device of claim 2, wherein the photocleavable linkages are receptive to photocleavage by an application of a double or multiple photon irradiation.

8. The optical device of claim 2, wherein the photocleavable linkages comprise a coumarin moiety, a nitrobenzyl-ether moiety, a nitroindoline-ether moiety, a p-hydroxyphenacyl moiety.

9. The optical device of claim 2, wherein the at least one hydrophilic (meth)acrylate polymer or copolymer and the at least one hydrophobic (meth)acrylate polymer or copolymer is prepared by copolymerizing (meth)acrylate monomers with one or more compounds having a structure:

where n is an integer in a range of from 1 to 100.

10. The optical device of claim 2, wherein the optical hydrogel composition is configured and suitable for use as an intraocular lens, a corneal inlay, a corneal ring, or a keratoprothesis in a human patient.

11. The optical device of claim 10, wherein the optical hydrogel composition has been positioned in the lens capsule of a patient.

12. The optical device of claim 2, wherein the separate regions are prepared by selectively irradiating an optical device comprising an initial optical hydrogel composition with a focused, near IR, visible, or UV light source; and
wherein the irradiating cleaves a portion of the photocleavable linkages, the cleavage providing separate regions of different crosslink densities which results in:
(a) a deformation or change of shape of the initial optical hydrogel composition; or
(b) a change of refractive index of the optical hydrogel composition.

13. The optical device of claim 12, wherein the cleavage results in change of refractive index of the optical hydrogel composition.

14. The optical device of claim 12, wherein the light source provides a two or multiple photon source.

15. The optical device of claim 2, wherein the separate regions of different crosslink densities of the optical device are defined by a three dimensional structure within the optical hydrogel composition.

16. The optical device of claim 2, wherein light source is a laser.

17. The optical device of claim 16, wherein the laser is suitable for use on a human patient when the optical device is implanted in an eye of the patient.

18. The optical device of claim 16, wherein the laser provides a pulse energy in a range of from about 0.05 nJ to 1000 nJ.

19. The optical device of claim 16, wherein the laser provides a pulse having a duration in a range of from about 1 femtosecond to about 500 femtoseconds.

20. A method of making the optical device of claim 2, the method comprising irradiating at least one region of an optical hydrogel composition with at least one wavelength of light in a range of from about 200 nm to about 1 micron, wherein the optical hydrogel composition comprises:
at least one hydrophilic (meth)acrylate polymer or copolymer and at least one hydrophobic (meth)acrylate polymer or copolymer, wherein the hydrophilic and/or hydrophobic polymer or copolymer are crosslinked with photocleavable linkages, wherein the photocleavable linkages comprise a coumarin moiety, a nitrobenzyl-ether moiety, a nitroindoline-ether moiety, or a p-hydroxyphenacyl moiety;
said optical hydrogel composition being transparent to at least one wavelength of light in a range of from about 200 to about 1000 nm; and said photocleavable linkages being receptive to cleavage with an application of at least one activating wavelength of light in a range of from about 200 nm and about 1000 nm; and wherein
so as to cleave a portion of the photocleavable linkages, resulting in the formation of separate regions of different crosslink densities within the hydrogel.

21. The method of claim 20, wherein cleaving the portion of the photocleavable linkages results in a re-distribution of water within the optical hydrogel composition.

22. The method of claim 20, wherein cleaving the portion of the photocleavable linkages results in a deformation or change of shape of the optical hydrogel composition.

23. The method of claim 20, wherein the cleaving the portion of the photocleavable linkages results in change of refractive index of the optical hydrogel composition.

24. The method of claim 20, wherein the irradiating light is provided by a laser.

25. The method of claim 20, wherein the irradiating light is provided by a multi-photon light source.

26. The method of claim 20, wherein the at least one irradiated region of the optical device defines a three dimensional structure within the optical hydrogel composition.

27. The method of claim 20, wherein the method is performed following the surgical insertion of the optical device in a human eye.

28. The method of claim 20, further comprising verifying a change in refractive index of the optical hydrogel composition.

29. The optical device of claim 2, wherein the optical hydrogel composition contains a three-dimensional pocket, channel, or layer in which the crosslink density is lower and the concentration of water is higher than in the rest of the optical hydrogel composition.

30. The optical device of claim 1, wherein the optical hydrogel composition contains water in an amount in a range from about 5 wt % to about 50 wt %, relative to the weight of the entire hydrogel composition.

31. The optical device of claim 1, wherein the at least one hydrophobic (meth)acrylate polymer or copolymer is derived from 2-phenylethyl-(meth)acrylate, methyl(meth)acrylate, or 3-phenylpropyl(meth)acrylate.

32. The optical device of claim 2, wherein the optical hydrogel composition contains water in an amount in a range from about 5 wt % to about 50 wt %, relative to the weight of the entire hydrogel composition.

33. The optical device of claim 2, wherein the at least one hydrophobic (meth)acrylate polymer or copolymer is derived from 2-phenylethyl-(meth)acrylate, methyl(meth)acrylate, or 3-phenylpropyl(meth)acrylate.

34. A method for modifying the refractive index of the optical device of claim 1, the method comprising irradiating at least one region of the optical hydrogel composition of claim 1 with at least one wavelength of light in a range of from about 200 nm to about 1 micron,
- so as to cleave a portion of the photocleavable linkages resulting in separate regions of different crosslink densities within the optical hydrogel containing different distributions of water,
- the composition being deformable upon cleavage of the photocleavable linkages and redistribution of water within the hydrogel.

35. The optical device of claim 2, wherein the photocleavable linkages comprise a coumarin moiety.

36. The optical device of claim 2, wherein the photocleavable linkages comprise a nitrobenzyl-ether moiety.

37. The optical device of claim 2, wherein the photocleavable linkages comprise a nitroindoline-ether moiety.

38. The optical device of claim 2, wherein the photocleavable linkages comprise a p-hydroxyphenacyl moiety.

* * * * *